United States Patent
Gabele et al.

(10) Patent No.: US 6,622,871 B2
(45) Date of Patent: Sep. 23, 2003

(54) PLATE-SHAPED FILTER HOLDER FOR A STERILIZING CONTAINER

(75) Inventors: Lorenz Gabele, Sauldorf (DE); Wolfgang Schwanke, Rietheim-Weilheim (DE)

(73) Assignee: Aesculap AG & Co. KG, Tuttlingen (DE)

( * ) Notice: Subject to any disclaimer, the term of this patent is extended or adjusted under 35 U.S.C. 154(b) by 29 days.

(21) Appl. No.: 09/766,681

(22) Filed: Jan. 18, 2001

(65) Prior Publication Data

US 2001/0020601 A1 Sep. 13, 2001

Related U.S. Application Data

(63) Continuation of application No. PCT/EP99/02682, filed on Apr. 21, 1999.

(30) Foreign Application Priority Data

Jul. 21, 1998 (DE) .......................................... 198 32 823

(51) Int. Cl.[7] .......................... B01D 24/12; B01D 29/05; B01D 35/30
(52) U.S. Cl. ........................ 210/455; 210/456; 210/463; 210/483; 210/495; 210/498; 422/101; 422/102; 422/104
(58) Field of Search ................................. 210/483, 495, 210/498, 450, 455, 456, 459, 463, 473, 477, 231, 232, 486.346, 488; 220/315, 326; 422/101, 102, 104

(56) References Cited

U.S. PATENT DOCUMENTS

| | | | | |
|---|---|---|---|---|
| 1,011,976 A | * | 12/1911 | Lithgow et al. | ............. 210/231 |
| 4,796,778 A | * | 1/1989 | Habig et al. | ................. 220/315 |
| 5,736,043 A | * | 4/1998 | Nichols et al. | ............. 210/477 |
| 5,925,247 A | * | 7/1999 | Huebbel | ................. 210/321.75 |

FOREIGN PATENT DOCUMENTS

| | | |
|---|---|---|
| DE | 37 10 049 | 10/1988 |
| DE | 3710049 | * 10/1988 |
| DE | 297 20 450 | 1/1998 |
| DE | WO-00/04933 | * 2/2000 |

* cited by examiner

Primary Examiner—W. L. Walker
Assistant Examiner—Marianne Ocampo
(74) Attorney, Agent, or Firm—Barry R. Lipsitz; Douglas M. McAllister

(57) ABSTRACT

The present invention involves a plate-shaped filter holder for use with a sterilizing container. The filter holder comprises a peripheral outer pressure rim, a central pressure region, a mounting device for fixing the filter holder on the sterilizing container and including webs between the outer pressure rim and the central pressure region which leave open breakthroughs therebetween. In order to prevent undesirable deformations in the filter holder, the webs extend at least partially in a direction which comprises a component in the peripheral direction.

16 Claims, 5 Drawing Sheets

Figure 1:
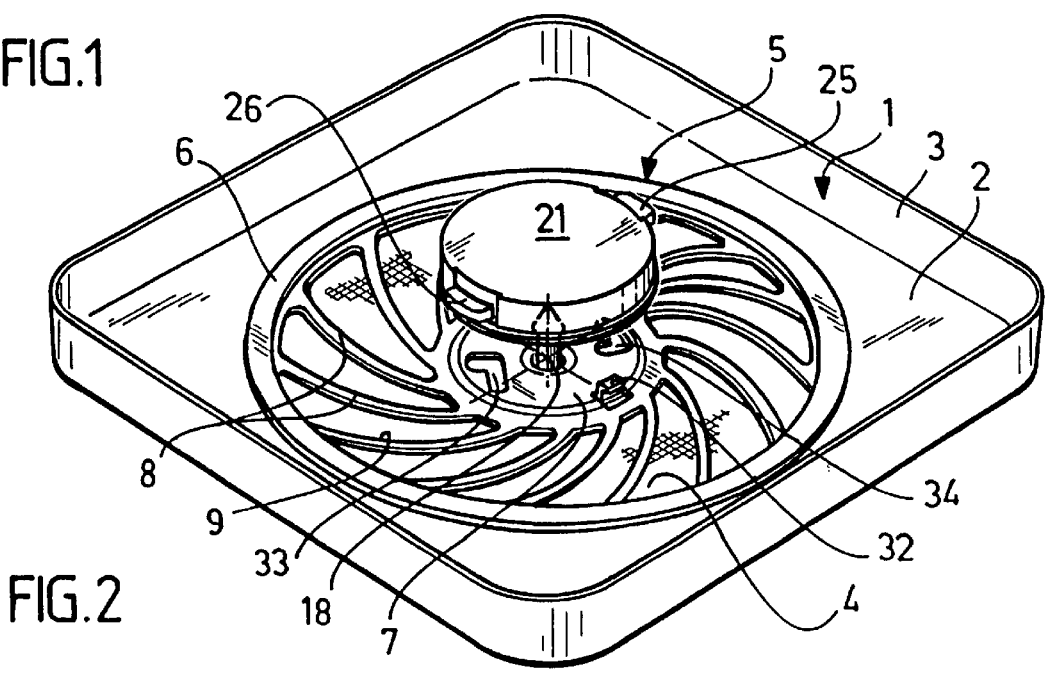

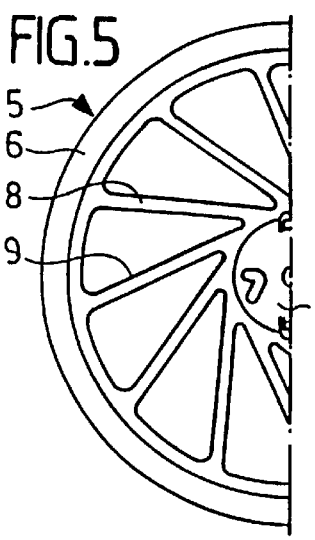
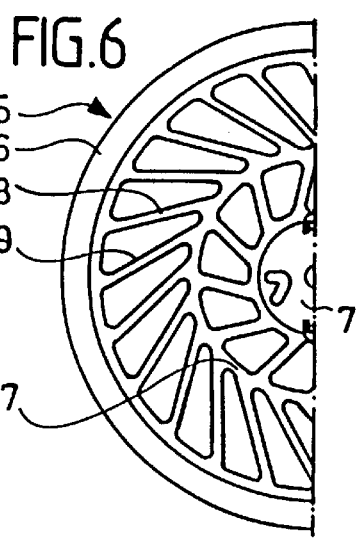
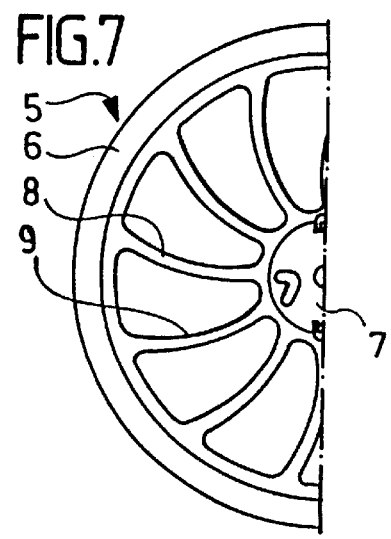
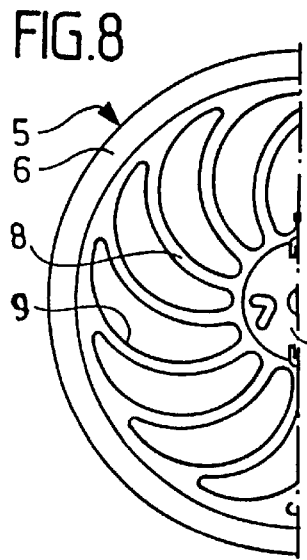
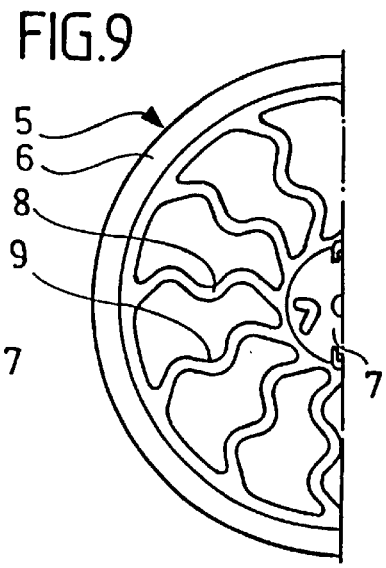
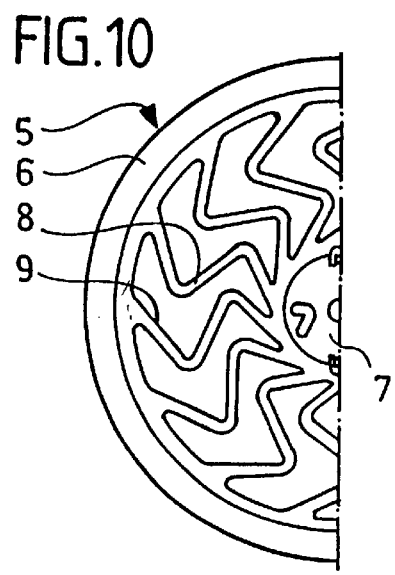
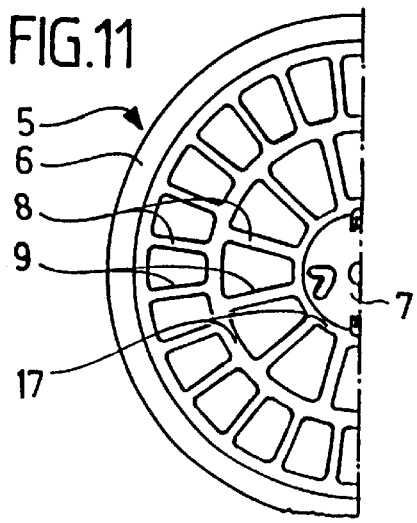
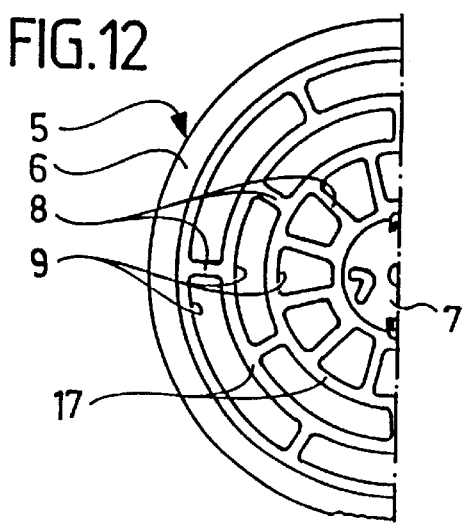

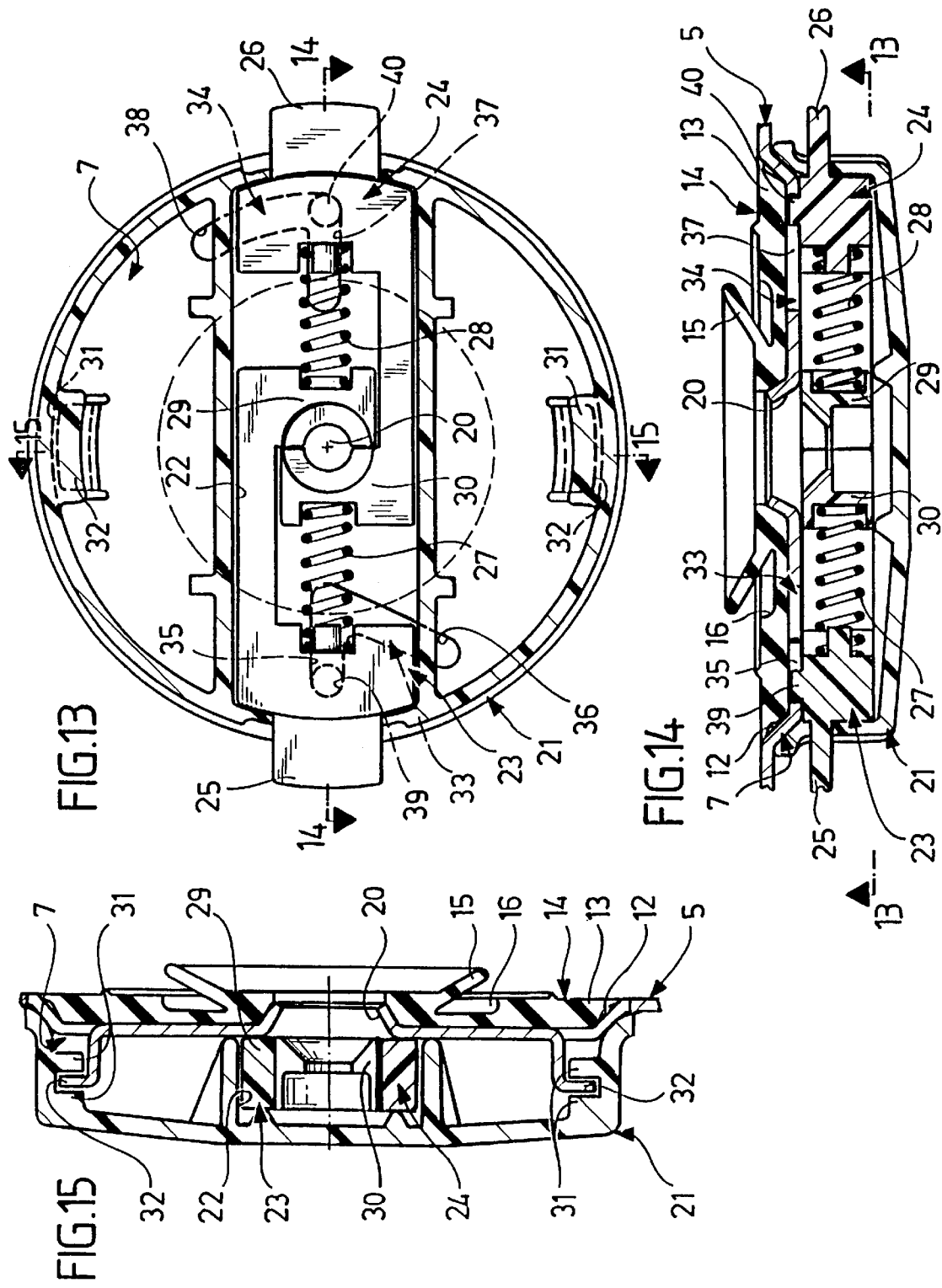

PLATE-SHAPED FILTER HOLDER FOR A STERILIZING CONTAINER

This application is a continuation of international application number PCT/EP99/02682 filed on Apr. 21, 1999. This application claims the benefit of German Patent Application No. 198 32 823.0 filed Jul. 21, 1998.

The invention relates to a plate-shaped filter holder for a sterilising container, including a peripheral outer pressure rim, a central pressure region, a mounting device for fixing the filter holder on the sterilising container, and including webs between the outer pressure rim and the central pressure region which leave open breakthroughs therebetween.

Such a filter holder for a sterilising container is known from DE 37 10 049 B1 for example. Extensive filter materials, for example paper filters or textile filters, can be pressed closely against breakthroughs in the sterilising container with the help of a plate-shaped filter holder, breakthroughs of this type being located in the lid of a sterilising container, in a side wall or in the base thereof for example. In order to fix the filter in position over a long period, it is necessary to press against the filter holder in a resilient manner and this is effected, in the case of the known arrangements, by means of a central mounting device which presses the filter holder against the filter bed by deforming it resiliently. In the case of the known filter holder, sealing is affected firstly by means of a seal around the outer pressure rim and secondly by means of a central seal in the central pressure region. In the known filter holders, the outer pressure rim is connected to the central pressure region by means of radial webs which leave open breakthroughs therebetween through which gas exchange can take place.

It has become apparent that stresses, which may lead to undesirable deformation of the filter holders, can occur in filter holders of this type. Such stresses occur, for example, when punching out the breakthroughs or during deep drawing processes by means of which the filter holder is formed into the desired shape. These undesirable deformations lead to the filter holder resting non-uniformly on the filter bed so that the sealing thereof cannot always be ensured. In order to prevent this, it is necessary to remove the distortions by subjecting the filter holders to an appropriate finishing process, for example by means of a heat treatment process.

The object of the invention is to construct a filter holder of the type described in the first part of claim 1 in such a manner that undesirable distortions are reliably prevented.

In accordance with the invention, this object is achieved in the case of a filter holder as described hereinabove in that the webs extend at least partially in a direction which comprises a component in the peripheral direction. surprisingly, it has been discovered that distortions will not occur if care is taken to ensure that the webs between the outer pressure rim and the central pressure region do not extend exactly in the radial direction, but rather that these webs extend a least partially in the peripheral direction or at least in a direction which has a component in the peripheral direction. By virtue of the webs extending in this manner, the material can flow continuously in the peripheral direction and should the production of stresses possibly occur, then stresses of this type will start to dissipate as soon as they occur. This is not possible in the case of webs which extend exclusively in the radial direction.

Geometrically, the webs may be very different in shape with the sole proviso however, that they have a component in the peripheral direction at least to a partial extent.

For example, provision may be made for the webs to extend between the central pressure region and the outer pressure rim in the form of curves.

It is also possible, for the webs to extend in straight lines between the central pressure region and the outer pressure rim whereby they then include an angle with the radial direction.

The webs may have a component acting in the same peripheral direction over their entire length, but in a modified embodiment it is also possible for the peripherally extending component of the web to alter its direction over the length of the web.

For example, the webs could extend in wave-like or zigzag form over their longitudinal extent.

In a particularly preferred embodiment, provision is made for the webs to compromise sections along their longitudinal extent which extend alternately radially and in the peripheral direction.

The webs may be in the form of independent components between the outer pressure rim and the central pressure region, but it is also possible for adjacent webs to be connected together by connecting webs. The stability of the filter holder will thereby be increased, but nevertheless undesirable distortions will be avoided because of the peripheral components in the path traced by the webs.

In a particularly preferred embodiment, provision is made for at least one middle web extending in the peripheral direction to be arranged between the central pressure region and the outer pressure rim, and for connecting webs having a radial component to be arranged between the middle web and the outer pressure rim, the inner pressure region or an adjacent middle web, said connecting webs being joined to opposite sides of the middle web and being mutually displaced in the peripheral direction. The connecting webs could extend, in particular, in the radial direction. One then obtains a construction in which radially extending webs do in fact extend between the central pressure region and the outer pressure rim, although they do not extend over the whole of the spacing between the outer pressure rim and the central pressure region, but rather, only over a partial region, namely up to the next middle web, and this middle web extends in the peripheral direction so that, in toto, the web connection between the outer pressure rim and the central pressure region extends alternately radially and in the peripheral direction. It is also ensured hereby that undesirable distortions are avoided.

In order to fix the filter material properly in place, it is expedient if a ring seal is held on the outer pressure rim and moreover, a resiliently deformable pressure seal may also be arranged on the central pressure region.

In a particularly preferred embodiment, this pressure seal is a lip seal having a resilient sealing lip which is adapted to be pressed onto the central pressure region. Such a sealing lip can be deformed to a relatively large extent, so that even with sealing materials of differing thickness, it is possible to ensure proper seating in the central region in every case, even when the spacing of the filter holder from the sterilising container is the same in every case. Tolerances in the spacing are accommodated by the great extent to which the sealing lip can be deformed.

It is expedient if the lip seal comprises an annular mounting body onto which the annular sealing lip is moulded.

In particular, provision may be made for the mounting body to comprise a recess into which the lip seal enters when it is pressed to the full extent against the central pressure region.

A particularly simple way of fixing this filter holder on the sterilising container ensues if, in accordance with a preferred embodiment, provision is made for the mounting device to comprise a housing having two locking bodies which are adapted to be resiliently displaced relative to one another in the peripheral direction and which engage behind a retaining member of the sterilising container, which projects through the filter holder, when in a non-displaced locking position but release it when in a displaced release position, for the housing to be adapted to be fixed to the filter holder in the central pressure region by a rotational movement in which respective projections and recesses on the filter holder and on the housing interlock, and for at least one releasable latch to be provided which prevents the housing from rotating relative to the filter holder when it is attached to the filter holder. Such a mounting device having two locking bodies which are adapted to be displaced relative to one another is known in the case of filter holders in accordance with the first part of claim 1 (DE 37 10 049 B1), but in this case, the housing is permanently connected to the filter holder, for example by means of rivets, screws, etc. In the case of the construction being described however, the housing is connected to the filter holder by a rotational movement similar to that of a bayonet connection, and it is prevented from being unintentionally released by virtue of the releasable latch. Consequently, it is possible to fix the housing on to the filter holder by means of the two locking bodies without using a tool and without using additional parts.

It is particularly advantageous hereby, if the latch is formed by one of the two locking bodies which prevents the housing from rotating when in its locking position and releases the housing when in its release position. In this embodiment it is not necessary to provide a separate latch, but rather, the locking body in the housing that is displaceable against spring force also takes on the task of a latch which prevents the housing from being unintentionally rotated and released.

Furthermore, is particularly advantageous if the other locking body prevents the housing from rotating when in its release position and releases it when in its locking position. It is thereby ensured that during the displacement of the locking body into its release position, i.e. the position in which the filter holder releases the retaining member of the sterilising container and can be removed from the sterilising container, the housing cannot be unintentionally rotated and removed from the filter holder. In order to rotate the housing, one of the two locking bodies must be displaced into the release position, whereas the other locking body must remain in the locking position. Consequently, rotation of the housing is not possible when both of the locking bodies are in the locking position, nor, when the two locking bodies are in the release position. Only these two positions will occur in normal operation of the filter holder since the two locking bodies are displaced from the locking position into the release position by diametrical pressure. On the other hand, if it is intended to rotate the housing relative to the filter holder so as to remove the housing, one must take deliberate care that only one of the two locking bodies is displaced.

Hereby, in a particularly preferred embodiment, provision is made for cam tracks and projections, which are guided therein, on the central pressure region and on the locking bodies respectively to co-operate and thereby allow the housing to rotate relative to the filter holder only in said certain positions of the locking bodies.

Thus, for example, provision may be made for one cam track for the locking body which secures the housing in its locking position to comprise a radially inwardly directed section, and, adjoined to the inner end of this section and adjacent thereto, an outwardly extending section. By having such a section, it is ensured that it is only possible to rotate the housing relative to the filter holder when the corresponding locking body has been moved into the release position.

Furthermore, it is expedient if one cam track for the locking body which secures the housing in its release position comprises a radially inwardly directed section, and a peripherally extending section adjoining the outer end of said first-mentioned section. Thus, this locking body only enables the housing to be rotated when it is itself in the locking position, whereas the housing is prevented from rotating relative to the filter holder in every other position.

In particular, provision may be made for the radially inwardly directed sections of the cam tracks and the projections engaging in the cam tracks to be arranged such that they are mirror symmetrical relative to the rotational axis of the housing. It is thereby possible to arrange the cam tracks and the projections such that the housing can be seated on the filter holder in two positions displaced by 180° whereby each of the two locking bodies can take on the role of that locking body, which prevents the housing from rotating in the release position or in the locking position, in dependence on the orientation at which the housing has been seated, i.e. one can utilise a completely symmetrical construction for the locking bodies and one does not have to be careful when seating the housing as to which projection engages in which cam track.

To this end, it is also expedient if the end points of the sections adjoining the radially inwardly directed sections are arranged such that they are mirror symmetrical relative to the rotational axis of the housing.

Figure 2:
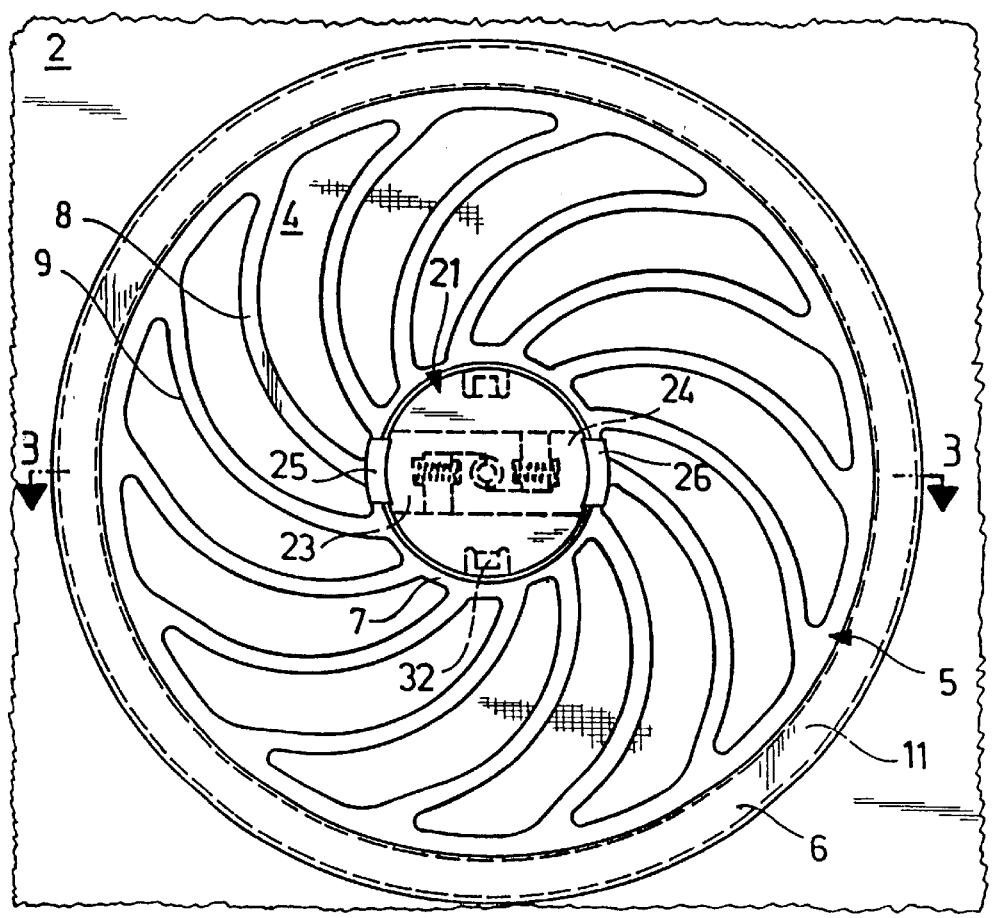
Figure 3:
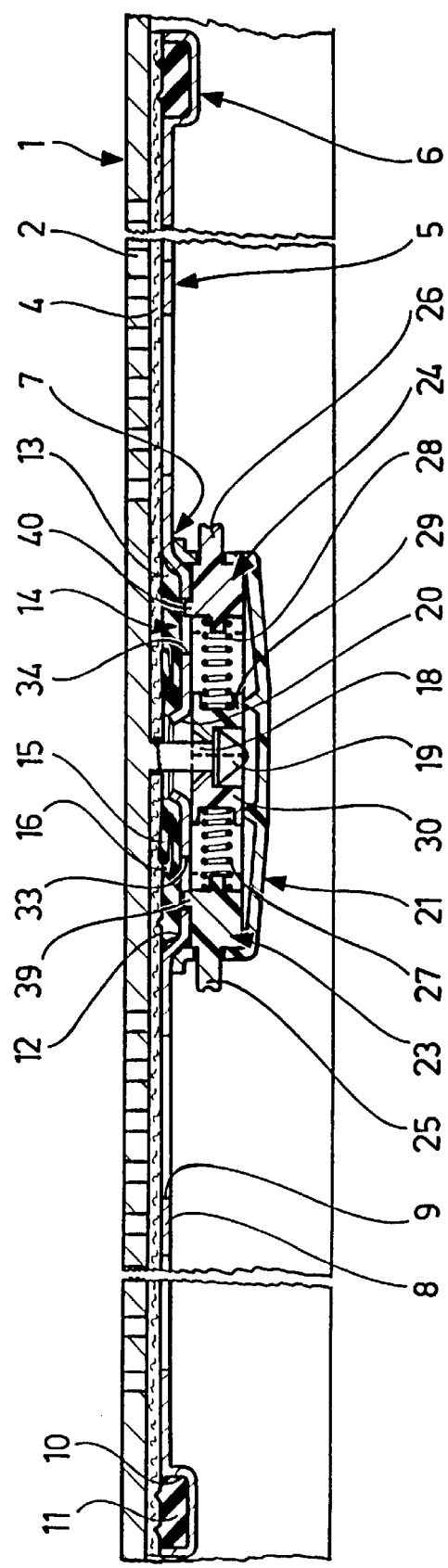
Figure 4:
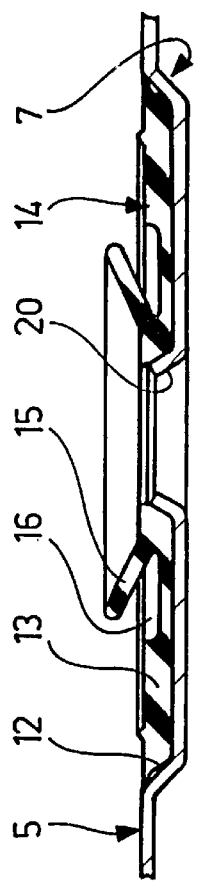
Figure 16:
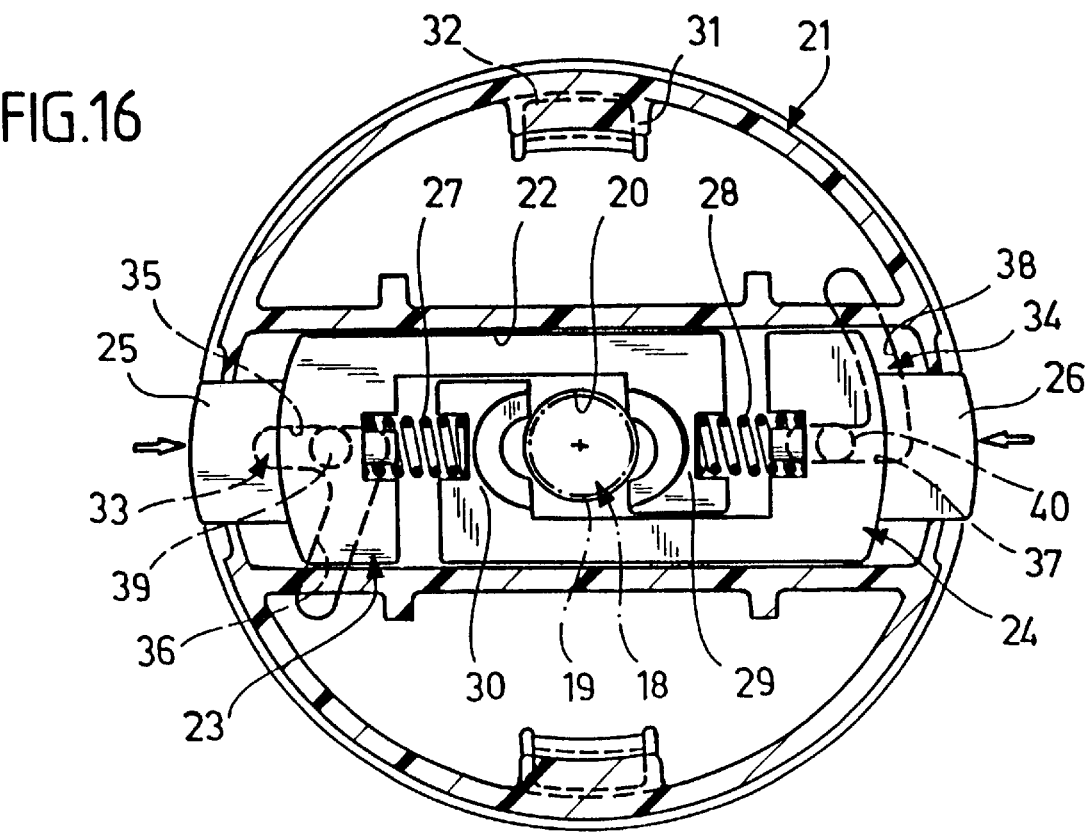
Figure 17:
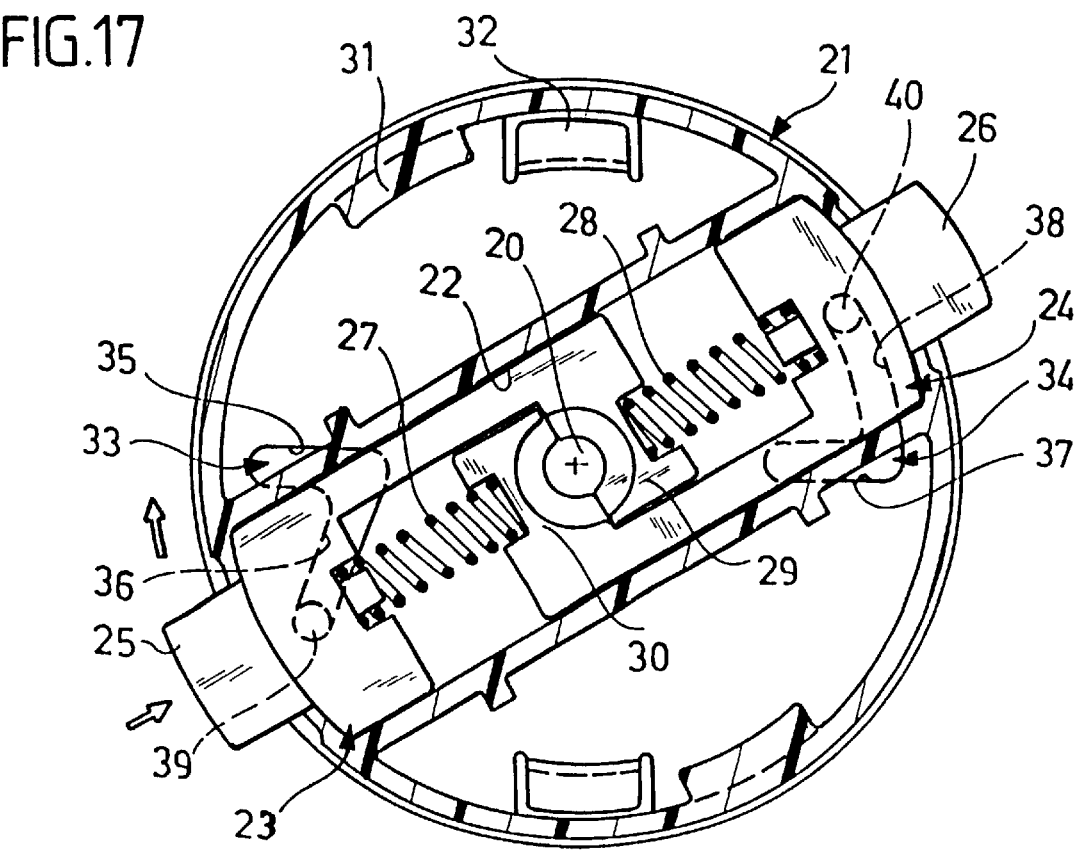

In conjunction with the drawing, the following description of preferred embodiments will serve for a more detailed explanation of the invention. Therein FIG. 1 shows a perspective view of the inner face of a lid for a sterilising container incorporating a filter holder having the housing for the mounting device removed;

FIG. 2 a top view of the filter holder in FIG. 1 wherein the housing for the mounting device is in place;

FIG. 3 a sectional view along the line 3—3 in FIG. 2;

FIG. 4 an enlarged detailed view of the central seal in place on the filter holder in a non-deformed state, FIG. 5 a partial view of another preferred embodiment of a filter holder having straight webs;

FIG. 6 a view similar to FIG. 5 having straight webs and a middle web;

FIG. 7 a view similar to FIG. 5 having curved webs;

FIG. 8 a view similar to FIG. 5 having curved webs flowing tangentially into the outer seating rim;

FIG. 9 a view similar to FIG. 5 having wave-like webs;

FIG. 10 a view similar to FIG. 5 having zigzag webs;

FIG. 11 a view similar to FIG. 5 having radial webs and a middle web;

FIG. 12 a view similar to FIG. 5 having radial webs and two middle webs;

FIG. 13 a cross sectional view along the line 13—13 in FIG. 14 of the housing for the mounting device having two locking bodies mounted therein;

FIG. 14 a sectional view along the line 14—14 in FIG. 13;

FIG. 15 a sectional view along the line 15—15 in FIG. 13;

FIG. 16 a sectional view similar to FIG. 13 having locking bodies displaced into the release position and FIG. 17 a view similar to FIG. 13 having a housing which is rotated relative to the filter holder and is adapted to be removed therefrom.

An inverted lid 1 of a sterilising container is illustrated in FIG. 1, said lid having a flat upper face 2 and a downwardly directed rim 3 adjoined thereto. The upper face 2 comprises breakthroughs which are covered by an extensive filter bed 4, for example by a filter paper or by a textile sheet filter.

This filter bed 4 is pressed against the inner face of the lid 1 by means of a filter holder 5, and for this purpose, this filter holder 5 comprises an annular outer pressure rim 6 and a central pressure region 7 which are connected together by means of webs 8 whereby breakthroughs 9 are formed between the webs 8 through which an exchange of gas can take place.

The pressure rim 6 has a U-shaped cross-section and thus forms an annular groove 10 into which an elastomeric ring seal 11 is placed.

An annular groove 12, which accommodates an annular body 13 of a central seal 14, is formed in the central pressure region 7. An annular sealing lip 15 is moulded onto the annular body 13, said sealing lip being inclined relative to the filter bed 4 and being capable of being bent resiliently against the annular body 13 and then sinking into an annular recess 16 in the annular body 13 (FIGS. 3 and 4). Consequently, the sealing lip 15 can bridge over relatively large sealing areas and can adapt to filter beds 4 of differing thicknesses.

In the embodiment illustrated in FIGS. 1 to 4, the webs 8 are curved whereby they have a component in the peripheral direction over their entire length i.e. parallel to the pressure rim 6, this component increasing from the interior the exterior.

This shaping of the webs 8 involving a significant component in the peripheral direction results in mechanical stresses in the filter holder 5 being avoided during the manufacture and also in the subsequent use thereof, whereby if such stresses should occur during manufacture, they can be balanced out by virtue of the described shaping of the webs 8.

The filter holder 5 may, for example, be manufactured from a metal plate in the form of a deep drawn part, the breakthroughs 9 being produced by a stamping process.

Other possible shapes for the webs 8 are illustrated in FIGS. 5 to 12. In FIG. 5, the webs 8 extend in straight lines from the interior to the exterior, although they have a significant component in the peripheral direction. Straight webs 8 are also provided in the embodiment shown in FIG. 6, however, in this case there are two different sets, namely, an inner set and an outer set which have respective peripheral components extending in opposite directions. The webs 8 of these two sets both flow into a middle web 17 extending concentrically relative to the outer pressure rim 6, namely, in such a manner that the points where the webs 8 of the outer set and those of the inner set flow into the middle web 17 are relatively displaced in the peripheral direction. This arrangement results in there being a connection between the central pressure region 7 and the outer pressure rim 6 which has a significant peripheral component throughout the whole area of the webs 8.

In the embodiment of FIG. 7, the webs 8 are curved, whereby they have a component in the peripheral direction in the region near the rim, the direction of this component being different from the component in the region near the centre.

In the embodiment of FIG. 8, the webs 8 are curved in similar manner to that in the embodiment of FIGS. 1 to 4, however they are more heavily curved than in the embodiment of FIG. 2 so that these webs 8 run into the outer pressure rim 6 in a substantially tangential manner.

In the embodiment of FIG. 9, the webs 8 have a wavelike shape, i.e. the directions of the components alternate in the peripheral direction.

The same applies in regard to the embodiment of FIG. 10 wherein the webs 8 are formed from adjoining straight sections which are angled relative to one another.

In the embodiment of FIG. 11, there is provided a concentric middle web 17 in a manner similar to the embodiment of FIG. 6, whereby the webs 8 are displaced relative to one another where they flow into the middle web. In contrast to the embodiment of FIG. 6 however, the webs 8 in this case extend exactly radially so that the component in the peripheral direction is formed by the middle web 17. The connecting lines from the central pressure region 7 to the outer pressure rim 6 extend in part over the radial webs 8 and in part over the middle web 17 which extends in the peripheral direction, so that, in toto, these connecting lines exhibit components in the peripheral direction in at least sections thereof whereby these components in the peripheral direction ensure that distortions can be avoided.

The embodiment of FIG. 12 generally corresponds to that of FIG. 11, but with the difference that, in this case, two concentric middle webs 17 are provided, these being connected to one another via three sets of radial webs 8. In this case too, the webs 8 are displaced relative to one another in the peripheral direction in the regions where they flow into the middle webs 17.

For the purposes of fixing the filter bed 4 onto the lid 1, the latter incorporates a vertically projecting spigot 18 having a head 19 which widens in step-like manner. This spigot 18 projects through a central opening 20 in the central pressure region 7 of the filter bed 4 and ends in a pot shape housing 21 which is connected to the filter holder 5 on the side thereof remote from the filter bed 4.

The housing 21 accommodates two locking bodies 23 and 24 which are located in a diametrical guideway 22 and are displaceable along this guideway, said locking bodies projecting out of the housing 21 in the form of push buttons 25 and 26 and being displaced into their maximum outer positions by means of compression springs 27 and 28 effective therebetween. In this position, the two locking bodies 23 and 24 engage around the spigot 18 by means of respective transverse arms 29, 30 and thereby engage under the step-like projecting head 19 of the spigot 18. The housing 21 is thereby fixed to the filter holder 5 in the axial direction at the spigot 18 and hence too, it is also fixed on the lid 1, namely, in a position in which the filter holder 5 is pressed against the inner face of the lid 1. Consequently, this position of the locking bodies 23 and 24 is referred to as the locking position.

The two locking bodies 23 and 24 can be pushed into the housing 21 by pressing on the push buttons 25 and 26 against the effects of the compression springs 27 and 28, their transverse arms 29 and 30 thereby disengaging from the spigot 18 and hence allowing the housing 21 and the filter holder 5 to be removed from the spigot 18 and thus too, from the lid 1. Consequently, this position of the locking bodies 23 and 24 is referred to as the release position.

Hereby, the construction has been selected such that it is only possible to remove the housing 21 and the filter holder 5 from the spigot 18 when both of these locking bodies 23 and 24 are pushed into the housing 21 in the same manner, whereas, if only one of the locking bodies is displaced into the release position, it is not possible to remove the housing and the filter holder.

On the inner wall of the housing 21 having the guided locking bodies 23 and 24 therein, there are provided two inwardly projecting projections 31 which engage under outwardly projecting projections 32 on the filter holder 5 and thereby fix the housing 21 to the filter holder 5. The engagement between the projections 31 and 32 can be released by rotating the housing 21 about a rotational axis extending concentrically relative to the spigot 18 whereby the housing 21 can be removed from the filter holder 5 as soon as the projections 31 and 32 are located next to one another (FIG. 17). Thus here, we are concerned with a bayonet type locking arrangement between the housing 21 and the filter holder 5.

In the central pressure region 7 of the filter holder 5, there are arranged two cam tracks 33 and 34 which are simply formed by means of slots in the central pressure region 7. The cam track 33 comprises a section 35 extending radially inwardly from the outside and a section 36 which adjoins the inner end of said first-mentioned section and from there is inclined outwardly, the other cam track 34 likewise comprising a radially inwardly directed section 37 and a section 38 which extends in the peripheral direction and adjoins the outer end of the section 37. Hereby, the respective radially inwardly directed sections 35 and 37 of the two cam tracks 33 and 34 are arranged such that they are mirror symmetrical relative to the spigot 18, whilst the sections 36 and 38 extend in the same peripheral direction and both of them end in positions which are likewise arranged such that they are mirror symmetrical relative to the spigot 18 (FIG. 13).

On the lower faces of the two locking bodies 23 and 24, there are provided downwardly directed studs 39 and 40, which are directed towards the open side of the housing 21 and project into the respective cam tracks 33 and 34.

In order to connect the housing 21 to the filter holder 5, the housing 21 with the locking bodies 23 and 24 mounted therein is initially placed on the central pressure region 7 of the filter holder 5 at an angular position in which the two studs 39 and 40 at the free ends of the sections 36 and 38 can project thereinto (FIG. 17). In this angular position, the projections 31 and 32 are located next to one another and do not overlap.

If the housing 21 is now rotated about the rotational axis concentric with the stud 18, then the projections 31 and 32 are moved into a position where they overlap (FIG. 16), i.e. the bayonet connector is locked. This is immediately possible, since, by virtue of this rotational movement, the stud 40 for the locking body 24 runs in the section 38 of the cam track 34 extending in the peripheral direction without the locking body 24 thereby been displaced relative to the housing 21. The stud 39 of the locking body 23 runs in the section 36 of the cam track 33 inclined to the centre and thereby displaces the locking body 23 against the effects of the two compression springs 27 and 28 until the innermost end of the radial section 35 of the cam track 33 is reached. The locking body 23 is then displaced radially outwards by the compression springs 27 and 28, the stud 39 then moves outwardly in the radial section 35 of the cam track 33 and thereby locks the housing 21 against rotation.

In this position, the housing 21 and the filter holder 5 are connected firmly together, if the two locking bodies 23 and 24 are displaced together into the release position in the manner described, the studs 39 and 40 run in the respective radial sections 35 and 37 of the cam tracks 33 and 34, and the housing 21 is thereby secured against undesirable rotation in every case. In the locking position, prevention of such rotation is effected by means of the locking body 23, whereas it is effected by the locking body 24 in the release position.

In order to release the bayonet connection between the housing 21 and the filter holder 5, it is necessary to push the locking body 23 alone into the housing 21 so as to thereby push the stud 39 of the locking body 23 up to the inner end of the section 35 of the cam track 33. It is only then that rotation of the housing 21 becomes possible, this then being directly effectable until the projections 31 and 32 are again located side by side in the manner illustrated in FIG. 17, whereby removal of the housing 21 becomes possible.

By virtue of the arrangement described, it is irrelevant as to which of the two locking bodies 23, 24 comes into contact with which of the cam tracks 33 and 34. The housing 21 and the locking bodies 23 and 24, together with the studs 39 and 40, are constructed in a fully symmetrical manner and the differing functions of the locking bodies 23 and 24 for securing the housing 21 against rotation are effected exclusively by means of the asymmetrical arrangement of the cam tracks 33 and 34. Consequently, the user is not forced to be careful in regards to the direction of the housing 21 when setting the housing 21 in place, it is sufficient to merely insert the studs 39 and 40 into the ends of the sections 36 and 38 when he is so doing.

What is claimed is:

1. A plate-shaped filter holder for use with a sterilizing container, said filter holder comprising:

a peripheral outer pressure rim, a central pressure region, a mounting device for fixing the filter holder on the sterilizing container, and a plurality of curved webs, each of which directly connects the outer pressure rim to the central pressure region leaving open breakthroughs therebetween, wherein:

the webs extend at least partially in a direction which comprises a component in the peripheral direction; and the webs extend in a rotationally symmetrical manner between the outer pressure rim and the central pressure region.

2. A filter holder in accordance with claim 1, wherein the mounting device comprises a housing having two diametrically opposite locking bodies which are adapted to be resiliently displaced relative to one another and which engage behind a retaining member of the sterilizing container, which said retaining member extends through the filter holder when in a non-displaced locking position but releases the filter holder when in a displaced release position, the housing is adapted to be fixed to the filter holder in the central pressure region by a rotational movement in which respective projections and recesses on the filter holder and on the housing respectively interlock, and at least one releasable latch is provided which prevents the housing from rotating relative to the filter holder when it is attached to the filter holder.

3. A filter holder in accordance with claim 2, wherein the latch is formed by one of the two locking bodies which prevents the housing from rotating when in its locking position and releases the housing when in its release position.

4. A filter holder in accordance with claim 3, wherein cam tracks and projections, which are guided therein, on the central pressure region and on the locking bodies respectively co-operate and thereby allow the housing to rotate relative to the filter holder only in said certain positions of the locking bodies.

5. A filter holder in accordance with claim 4, wherein the radially inwardly directed sections of the cam tracks and the projections engaging in the cam tracks are arranged such that they are mirror symmetrical relative to the rotational axis of the housing.

6. A filter holder in accordance with claim 4, wherein the end points of the sections adjoining the radially inwardly directed sections are arranged such that they are mirror symmetrical relative to the rotational axis of the housing.

7. A filter holder in accordance with claim 4, wherein one cam track for the locking body which secures the housing in its locking position comprises a radially inwardly directed section, and, adjoined to this section at the inner end thereof, an outwardly extending section adjacent to said first-mentioned section.

8. A filter holder in accordance with claim 4, wherein one cam track for the locking body which secures the housing in its released position comprises a radially inwardly directed section, and a peripherally extending section adjoining the outer end of said first section.

9. A filter holder in accordance with claim 3, wherein the other locking body prevents the housing from rotating when in its release position and releases the housing when in its locking position.

10. A filter holder in accordance with claim 1, wherein a resiliently deformable pressure seal is arranged on the central pressure region.

11. A filter holder in accordance with claim 10, wherein the pressure seal is a lip seal having a resilient sealing lip which is adapted to be pressed onto the central pressure region.

12. A filter holder in accordance with claim 11, wherein the lip seal comprises an annular mounting body onto which the annular sealing lip is moulded.

13. A filter holder in accordance with claim 12, wherein the mounting body comprises a recess into which the lip seal enters when it is pressed to the full extent against the central pressure region.

14. A filter holder in accordance with claim 1, wherein the webs have a component acting in the peripheral direction over their entire length.

15. A filter holder in accordance with claim 1, wherein the peripherally extending component of the web alters its direction over the length of the web.

16. A filter holder in accordance with claim 1, wherein a ring seal is held on the outer pressure rim.

* * * * *

UNITED STATES PATENT AND TRADEMARK OFFICE
CERTIFICATE OF CORRECTION

PATENT NO. : 6,622,871 B2
DATED : September 23, 2003
INVENTOR(S) : Gabele et al.

It is certified that error appears in the above-identified patent and that said Letters Patent is hereby corrected as shown below:

Column 9,
Line 1, change "4" to -- 5 --.

Signed and Sealed this

Thirtieth Day of December, 2003

JAMES E. ROGAN
*Director of the United States Patent and Trademark Office*